United States Patent
Jahn et al.

(10) Patent No.: US 9,475,056 B2
(45) Date of Patent: Oct. 25, 2016

(54) HOMOGENIZATION TUBES WITH FLOW DISRUPTERS FOR BEADLESS INTERRUPTED FLOW

(71) Applicant: OMNI INTERNATIONAL, INC., Kennesaw, GA (US)

(72) Inventors: Karl Jahn, Kennesaw, GA (US); Voya Vidakovic, Marietta, GA (US); John Hancock, Atlanta, GA (US); Thomas Gray, Canton, GA (US)

(73) Assignee: OMNI INTERNATIONAL, INC., Kennesaw, GA (US)

(*) Notice: Subject to any disclaimer, the term of this patent is extended or adjusted under 35 U.S.C. 154(b) by 0 days.

(21) Appl. No.: 14/840,533

(22) Filed: Aug. 31, 2015

(65) Prior Publication Data
US 2015/0367351 A1 Dec. 24, 2015

Related U.S. Application Data

(63) Continuation of application No. 14/590,656, filed on Jan. 6, 2015.

(60) Provisional application No. 61/923,845, filed on Jan. 6, 2014.

(51) Int. Cl.
*B02C 17/06* (2006.01)
*B02C 17/14* (2006.01)
(Continued)

(52) U.S. Cl.
CPC ............. *B02C 17/06* (2013.01); *B01F 5/0688* (2013.01); *B01F 11/0022* (2013.01); *B01L 3/502* (2013.01);
(Continued)

(58) Field of Classification Search
CPC ... B02C 17/06; B01L 9/06; B01L 2300/0832
USPC ........................................ 241/168, 169, 175
See application file for complete search history.

(56) References Cited

U.S. PATENT DOCUMENTS

| 1,878,924 A | 9/1932 | Will |
| 2,021,011 A | 11/1935 | Lande |

(Continued)

FOREIGN PATENT DOCUMENTS

| CN | 102399618 | 4/2012 |
| EP | 1521637 | 1/2004 |
| EP | 2318128 | 1/2010 |

OTHER PUBLICATIONS

International Search Report and Written Opinion; Date of Mailing: May 1, 2015; For PCT/US15/010307; 10 pgs.

*Primary Examiner* — Mark Rosenbaum
(74) *Attorney, Agent, or Firm* — Gardner Groff Greenwald & Villanueva, PC

(57) ABSTRACT

A flow disrupter in a tube chamber of a tube assembly for homogenizing sample materials includes a flow-disrupting body that extends generally transversely into the tube chamber and divides the tube chamber into two sub-chambers. The flow-disrupting body includes at least one narrowed flow passageway through which the sample flows back and forth in both axially reciprocating directions as the tube assembly is vigorously shaken at high speeds faster and more reliably than what can be accomplished by hand shaking. And the flow-disrupting body includes at least two flow-interrupting surfaces facing generally in opposite axial directions and against which the sample impacts in each respective axially reciprocating direction as the tube assembly is vigorously shaken. In this way, the vigorous high-speed shaking of the tube assembly including the flow disrupter results in significant particle-size reduction of the sample by mechanical shear, fluid shear, cavitation, and/or pressure differentials.

20 Claims, 10 Drawing Sheets

(51) Int. Cl.
 B01F 11/00 (2006.01)
 B01L 3/00 (2006.01)
 B01F 5/06 (2006.01)
 G01N 1/38 (2006.01)
 B01L 9/06 (2006.01)

(52) U.S. Cl.
 CPC .............. B01L 3/508 (2013.01); B01L 3/5635 (2013.01); B01L 9/06 (2013.01); B02C 17/14 (2013.01); G01N 1/38 (2013.01); *B01L 3/5082* (2013.01); *B01L 2300/087* (2013.01); *B01L 2300/0832* (2013.01)

(56) References Cited

U.S. PATENT DOCUMENTS

| | | | |
|---|---|---|---|
| 2,210,448 A | 8/1940 | Dodge | |
| 2,775,350 A | 12/1956 | Jones | |
| 3,300,051 A | 1/1967 | Mitchell | |
| 3,432,149 A | 3/1969 | Stalberg et al. | |
| 3,526,391 A | 9/1970 | Church | |
| 3,578,293 A | 5/1971 | Oberli | |
| 4,632,761 A | 12/1986 | Bowers et al. | |
| 4,818,114 A | 4/1989 | Ghavi | |
| 5,356,814 A | 10/1994 | Carrico, Jr. et al. | |
| 5,358,330 A | 10/1994 | Moll | |
| 5,501,841 A | 3/1996 | Lee et al. | |
| 5,547,275 A | 8/1996 | Lillelund et al. | |
| 5,556,544 A | 9/1996 | Didier | |
| 5,725,500 A | 3/1998 | Micheler | |
| 5,869,329 A | 2/1999 | Berndt | |
| 5,925,250 A | 7/1999 | Rocha | |
| 6,063,340 A | 5/2000 | Lewis et al. | |
| 6,401,552 B1 | 6/2002 | Elkins | |
| 6,799,884 B2 | 10/2004 | Sentmanat | |
| 6,880,771 B2 * | 4/2005 | Deppermann | B02C 17/14 241/175 |
| 7,182,912 B2 | 2/2007 | Carey et al. | |
| 8,016,218 B1 | 9/2011 | Friedman | |
| 2003/0146313 A1 | 8/2003 | Depperman | |
| 2006/0133957 A1 | 6/2006 | Knapp et al. | |
| 2010/0020632 A1 | 1/2010 | Corominas | |
| 2013/0217010 A1 | 8/2013 | Suchocki et al. | |
| 2014/0269160 A1 | 9/2014 | Chee Mun | |

\* cited by examiner

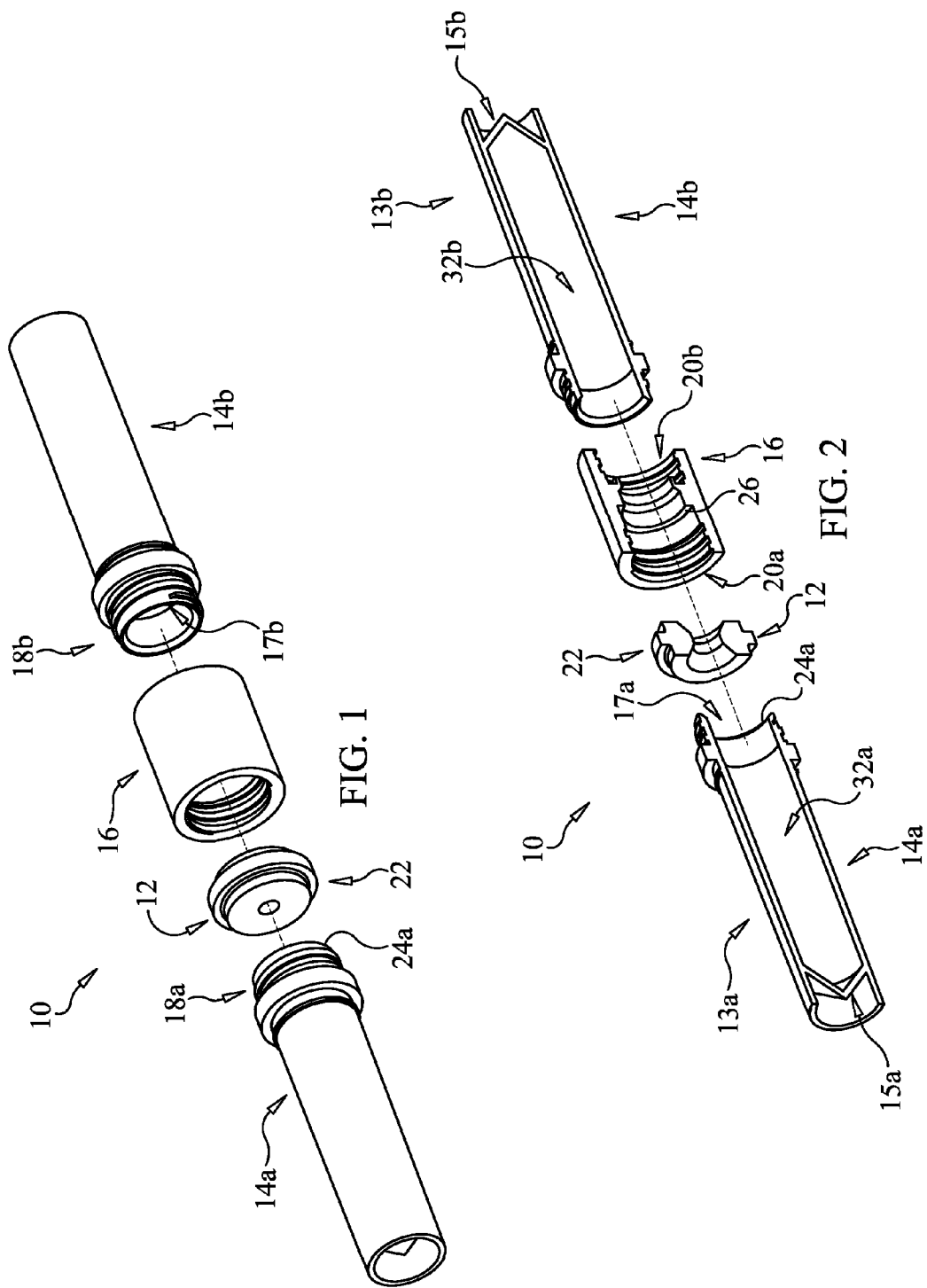

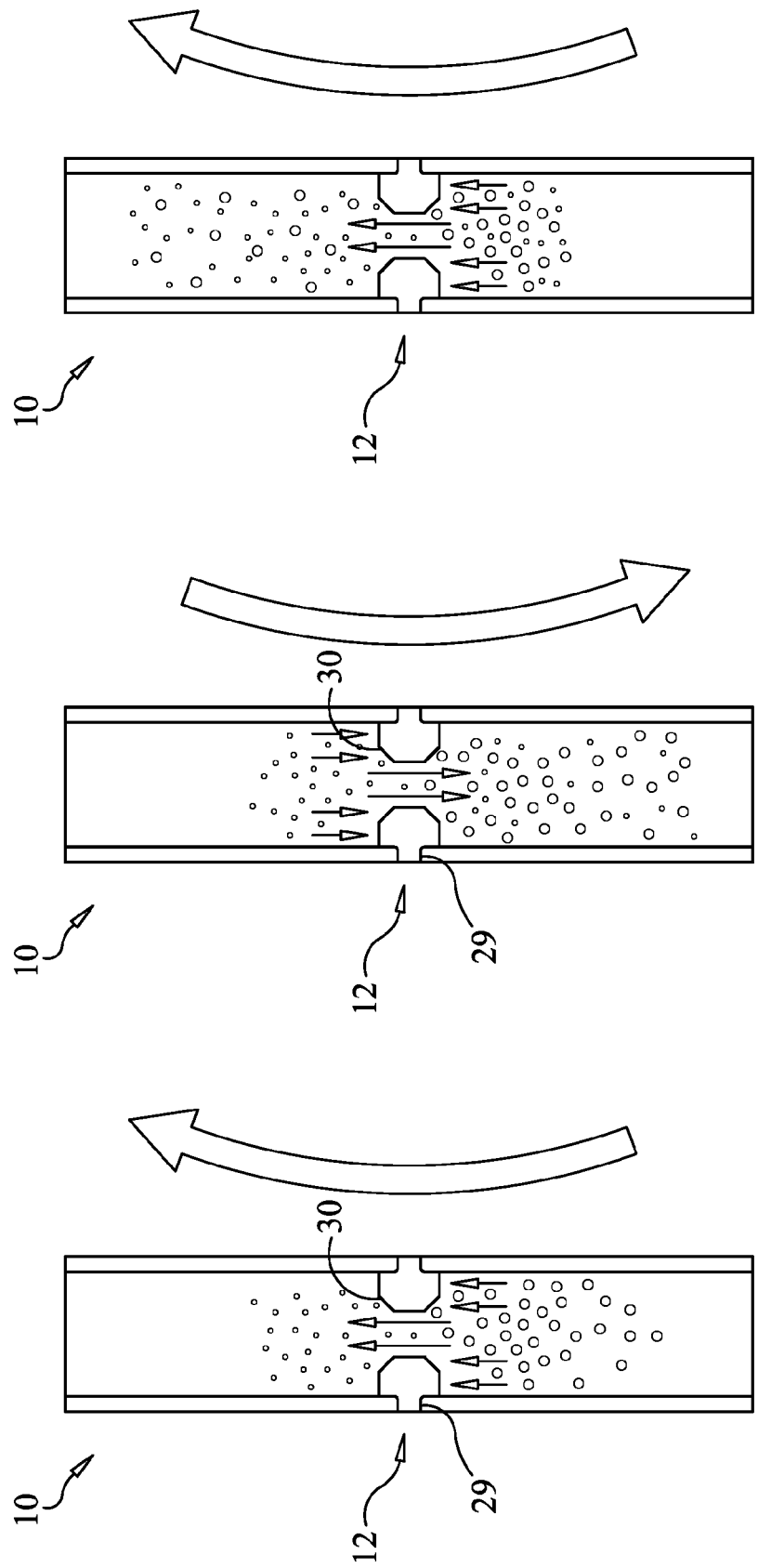

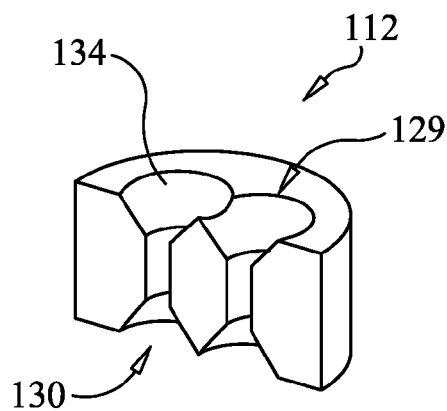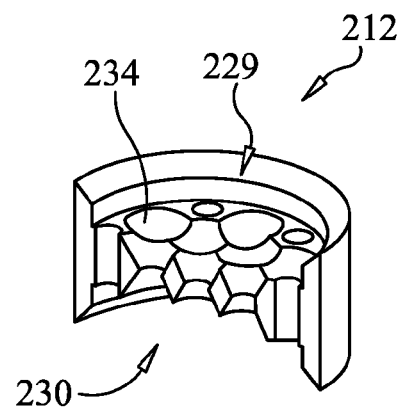
FIG. 8  FIG. 9
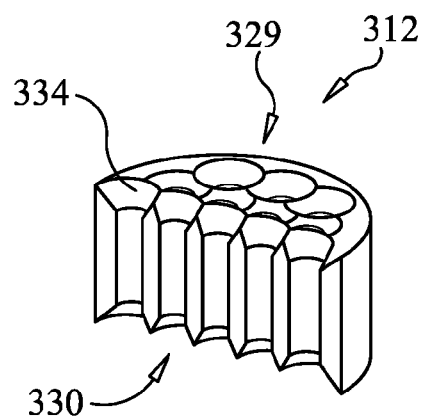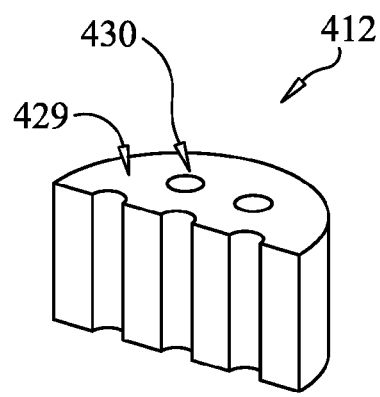
FIG. 10  FIG. 11

HOMOGENIZATION TUBES WITH FLOW DISRUPTERS FOR BEADLESS INTERRUPTED FLOW

CROSS-REFERENCE TO RELATED APPLICATION

This application is a continuation of U.S. Non-Provisional patent application Ser. No. 14/590,656, filed Jan. 6, 2015, which claims the priority benefit of U.S. Provisional Patent Application Ser. No. 61/923,845, filed Jan. 6, 2014, both of which are hereby incorporated herein by reference.

TECHNICAL FIELD

The present invention relates generally to laboratory devices and accessories for homogenizing sample materials, and particularly to tubes for containing samples and beads and for being shaken by high-powered, mechanical-shear, shaker-mill homogenizers to homogenize the samples.

BACKGROUND

Homogenization involves disaggregating, mixing, re-suspending, or emulsifying the components of a sample using a high-shear process with significant micron-level particle-size reduction of the sample components. Homogenization is commonly used for a number of laboratory applications such as creating emulsions, reducing agglomerate particles to increase reaction area, cell destruction for capture of DNA material (proteins, nucleic acids, and related small molecules), DNA and RNA amplification, and similar activities in which the sample is bodily tissue, bodily fluid, organic plant matter, and/or or another substance. Conventional laboratory equipment for such homogenizing applications includes shaker-mill homogenizing devices. Such shaker-mill homogenizing devices are commercially available for example under the brand name BEADRUPTOR (Omni International, Inc. of Kennesaw, Ga.).

Typical shaker-mill homogenizing devices include a swash plate holding a number of tubes containing the samples and a base unit that generates and transmits a "swashing" motion to the swash plate to homogenize the samples in the tubes using very large sinusoidal forces to vigorously shake the tubes at very high oscillatory rates. The shaking motion of the tubes is a back-and-forth axially reciprocating motion, which can be precisely linear or generally linear with a relatively small curve (the typical swashing action produces a slight arc in the travel path of the tubes in the radial and tangential planes of the swash plate). These high-powered, mechanical-shear, homogenizing devices typically operate at very high speeds of about 0.8 m/s to about 10.0 m/s to process per-tube volumes of about 0.025 mL to about 50 mL. Grinding media, typically a plurality of beads, are included in each tube to increase agitation during processing and thereby reduce the particle size of the sample. As such, these homogenizing devices are commonly referred to as "bead mills."

After processing, the homogenized sample and the grinding media must be separated. This separation step requires time and/or special equipment that result in increased costs. Additionally, post-separation sample-recovery yields are less than 100 percent due to unrecoverable portions of the sample that are left behind on the grinding media. But without the grinding media, many samples cannot be processed at all given the very-significant forces required to break down the sample particle size.

Accordingly, it can be seen that needs exist for improvements in sample processing with shaker-mill homogenizing devices to address the time and cost problem of post-processing separation of the sample and the grinding media without sacrificing the high homogenizing energies provided by the grinding media. It is to the provision of solutions to these and other problems that the present invention is primarily directed.

SUMMARY

Generally described, the present invention relates to a flow disrupter in a tube chamber of a tube assembly for homogenizing sample materials. The flow disrupter includes a flow-disrupting body that extends generally transversely into the tube chamber and divides the tube chamber into two sub-chambers. The flow-disrupting body includes at least one narrowed flow passageway through which the sample flows back and forth in both axially reciprocating directions as the tube assembly is vigorously shaken at high speeds faster and more reliably than what can be accomplished by hand shaking. And the flow-disrupting body includes at least two flow-interrupting surfaces facing generally in opposite axial directions and against which the sample impacts in each respective axially reciprocating direction as the tube assembly is vigorously shaken. In this way, the vigorous high-speed shaking of the tube assembly including the flow disrupter results in significant particle-size reduction of the sample by mechanical shear, fluid shear, cavitation, and/or pressure differentials.

In some example embodiments, the flow-disrupting body defines one or multiple flow passageways, in linear, helical, or other configurations. In some example embodiments, the flow-disrupting body defines one or multiple impact surfaces generally facing each axial direction, with the impact surfaces including perpendicular and/or ramped surfaces. The ramped impact surfaces of some embodiments are generally conical surrounding the flow passageways, those of some embodiments are axially extending fins, those of some embodiments are generally helically arranged fins, and those of some embodiments include generally transverse flow openings.

In some example embodiments the flow-disrupter is an insert for installing in a tube assembly, and in some embodiments it is integrally formed as part of the tube assembly or an adapter. In some example embodiments one flow-disrupter is provided for each tube assembly, and in some embodiments multiple flow-disrupters are provided for dividing the tube assembly into more than two sub-chambers. In some example embodiments the tube assembly includes two conventional tube containers (without their conventional endcaps) and an adapter for coupling them together, in some example embodiments the tube assembly includes one conventional tube container (without its conventional endcap) and a modified-longer endcap that couple together, and in some embodiments the tube assembly includes one conventional tube container, one conventional endcap, and an elongated adapter for coupling them together.

The specific techniques and structures employed to improve over the drawbacks of the prior systems and accomplish the advantages described herein will become apparent from the following detailed description of example embodiments and the appended drawings and claims.

BRIEF DESCRIPTION OF THE DRAWINGS

FIG. 1 is an exploded/unassembled perspective view of a sample tube assembly with an adapter and a flow disrupter according to a first example embodiment of the invention, for use with a shaker-mill homogenizer to produce beadless interrupted homogenizing flow.

FIG. 2 is a longitudinal cross-section view of the tube assembly with the adapter and the flow disrupter of FIG. 1.

FIG. 5 is a schematic view of with the tube assembly with the adapter and the flow disrupter of FIG. 1 in use being shaken in a first generally axial direction to homogenize the sample.

FIG. 6 shows the tube assembly with the adapter and the flow disrupter of FIG. 5 in use being shaken in a second/opposite generally axial direction to homogenize the sample.

FIG. 7 shows the tube assembly with the adapter and the flow disrupter of FIG. 6 in use being shaken in the first opposite generally axial direction to continue the reciprocating cycle to homogenize the sample.

FIG. 8 is a cross-sectional perspective view a flow disrupter according to a second example embodiment of the invention.

FIG. 9 is a cross-sectional perspective view a flow disrupter according to a third example embodiment of the invention.

FIG. 10 is a cross-sectional perspective view a flow disrupter according to a fourth example embodiment of the invention.

FIG. 11 is a cross-sectional perspective view a flow disrupter according to a fifth example embodiment of the invention.

DESCRIPTION OF EXAMPLE EMBODIMENTS

Figure 3:
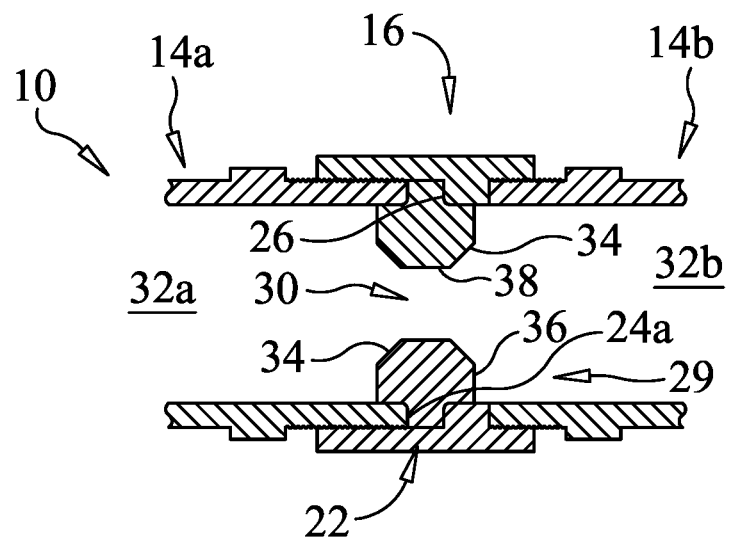
FIG. 3 is a side view of a portion of the tube assembly with the adapter and the flow disrupter of FIG. 2.
Figure 4:
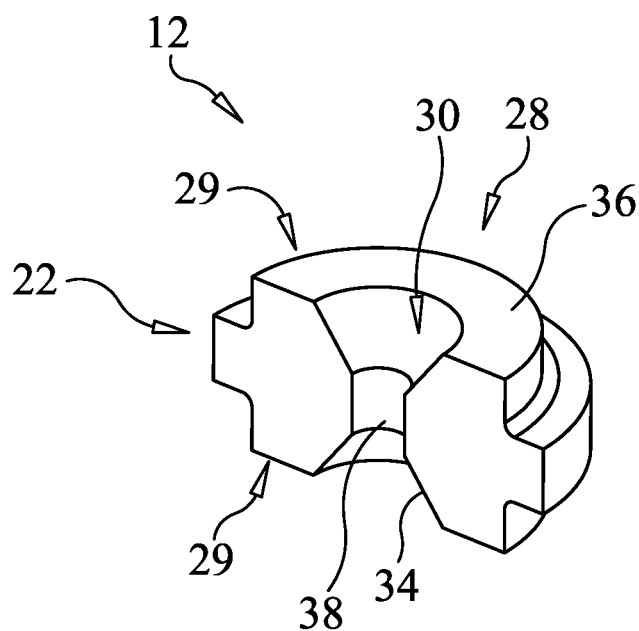
FIG. 4 is a cross-sectional perspective view of the flow disrupter of FIG. 1.

The present invention relates to homogenization of samples using for example conventional shaker-mill (aka bead-mill) homogenizers and using tube assemblies adapted to provide beadless disrupted flow of the samples. In particular, the tube assemblies are provided with internal flow-interrupting surfaces and flow-constricting passageway(s) to produce the same high homogenizing energy levels generated when homogenizing using beads, but without using any beads or other grinding media in the tube assemblies. As such, the tube assemblies can be used to homogenize samples that previously could only be homogenized using grinding media. Without the grinding media present, there is nothing in the tube assembly that the sample needs to be separated from after homogenization, so the separation step and cost are eliminated and the amount of sample recovered is increased. And because there are no beads and thus no bead-on-bead collisions during homogenization, there is no resulting bead chipping and heat generation. So there are no bead chips in the homogenized sample and the sample is heated less during homogenizing.

A few preliminary definitions are as follows. "Homogenizing" and "processing" as used herein are intended to be broadly construed to mean particle-size reduction of a sample by high-shear disaggregating, mixing, re-suspending, and/or emulsifying (i.e., separation, not destruction) of the components of the sample by an axially reciprocating shaking motion of the tubes containing the samples. "Homogenizer" and "homogenizing device" as used herein are intended to be broadly construed to include any type of device that homogenizes/processes samples, including not just the high-powered shaker-mill laboratory homogenizer described herein but also other laboratory equipment that is operable for homogenizing. "Sample" as used herein is intended to be broadly construed to include any type of material that can be homogenized and for which homogenization could be useful, such as but not limited to human and/or non-human bodily fluid and/or tissue (e.g., blood, bone-marrow cells, a coronary artery segment, or a piece of an organ), other organic matter (e.g., plants or food), and/or other chemicals. And "tube" and "tube assembly" are intended to be broadly construed to include any closable vessel that can hold a sample during homogenization and are not limited to conventional clear, plastic, cylindrical vials, so this term includes conventional sample tubes as well as the modified ones disclosed therein.

In example embodiments, the invention includes a flow disrupter that divides a tube chamber into two sub-chambers and that has at least one flow-constricting axial passageway and at least two flow-interrupting impact surfaces for sample-flow disruption during reciprocating sample flow between the sub-chambers. In one aspect, the flow disrupter invention is an insert that is provided by itself and that can be inserted into an existing tube container. In another aspect, the invention is a kit including a plurality of the flow-disrupter inserts with differently configured impact surfaces and/or flow passageways for customized selection of a particular one of the flow-disrupter inserts for homogenizing a particular sample. In yet another aspect, the invention is a tube assembly provided with the flow-disrupter insert. In still another aspect, the invention is an adapter for a tube assembly to permit using the flow-disrupter insert with two conventional tube containers. In yet still another aspect, the invention is an adapter for a tube assembly to permit using two conventional tube containers, with the adapter integrally including the flow disrupter. In still a further aspect, the invention is a tube assembly integrally including the flow disrupter. And in yet still another aspect, the invention is a method of homogenizing a sample using a tube assembly including the flow disrupter for sample-flow disruption during reciprocating sample flow between the sub-chambers.

Referring to the drawings, FIGS. 1-7 show a sample tube assembly 10 including a flow disrupter 12 according to a first example embodiment of the present invention. The tube assembly 10 includes two container shell components 14a and 14b together forming an internal chamber. And the flow disrupter 12 is positioned within the tube chamber to divide it into two sub-chambers. The flow disrupter 12 includes special geometry to disrupt the flow of the sample within the tube assembly 10 during reciprocating sample flow between the sub-chambers to significantly reduce particle size of the sample without using grinding beads or other grinding media.

Referring particularly to FIGS. 1-4, the tube assembly 10 of this embodiments includes two containers 14a and 14b (collectively, the containers 14) and an adapter 16 that removably couples the two containers together. Each container 14 has a peripheral sidewall (e.g., cylindrical or polygonal shaped), a closed end (e.g., a conical or flat bottom wall), and an open end (e.g., a top access opening). (The peripheral sidewalls 13a and 13b are collectively referred to as the peripheral sidewalls 13, the closed end-walls 15a and 15b are collectively referred to as the closed endwalls 15, and the access openings 17a and 17b are collectively referred to as the access openings 17.) The containers 14 can be provided in standard volumes of for example about 0.025 mL to about 50 mL, or in other volumes as may be desired. As examples for context, a conventional 1.5 mL tube container typically has a length of about 4.0 cm and a diameter of about 1.0 cm, and a conventional 30 mL tube container 14 typically has a length of about 8.0 cm and a diameter of about 3.0 cm.

The containers 14 and the adapter 16 include coupling elements that removably connect together, such as mating screw threads for screwing the containers and the adapter together into a single tube assembly 10 for homogenizing use and unscrewing them after use to remove the sample. In the depicted embodiment, for example, the containers 14 include external/male screw threads 18a and 18b (collectively, the container screw threads 18) at their open ends 17, and the adapter 16 includes mating internal/female screw threads 20a and 20b (collectively, the adapter screw threads 20) at both ends. In other embodiments, the coupling elements are provided by other (non-screw-threaded) twist-lock elements, clamps, pins, latches, or other coupling elements that removably connect together the containers and the adapter securely for sample processing.

In the depicted embodiment, the containers 14 are identical and provided by conventional sample tube containers, with their tube endcaps removed and not needed. As such, when two of the containers 14 are coupled together by the adapter 16, the overall length of the tube assembly 10 is about twice that of conventional tube assemblies of the same type and size (i.e., about twice the length of the conventional tube vessel including its endcap). And thus the screw threads 20 of the adapter 16 are identical to those of the unused endcaps.

In other embodiments, the tube assembly is provided by a conventional tube assembly including a conventional tube container and a conventional tube endcap. As such, one of the container shell components need not be a vessel that actually contains the sample but rather it can merely be a closure or other portion of the overall tube assembly. Accordingly, references herein to a tube assembly and to two container shell components are intended to be broadly construed to mean a vessel that can be opened to insert the sample, closed to contain the sample for processing, and reopened to remove the processed sample.

The adapter 16 removably connects the two containers 14 together with a good seal to retain the sample therein during processing. As such, the adapter 16 can be made of the same or a similar material as the containers 14, for example hard plastic. In typical embodiments such as that depicted, the adapter 16 is in the form of a hollow sleeve with its internal/female screw threads 20 at its opposite ends for mating with the external/male screw threads 18 of the containers 16.

The flow disrupter 12 is secured in place sandwiched between the adapter 16 and one of the containers 14 so that it extends radially inward into the tube assembly 10. In the depicted embodiment, for example, the flow disrupter 12 includes an outer mounting flange 22 that is pinched/captured between the peripheral edge 24a of the open end 17a of the container 14a (axially beyond its male screw threads 18a) and an internally flanged seat 26 of the adapter 16, with the seat positioned axially inward between the adapter screw threads 20. The disrupter mounting flange 22, the container open-end peripheral edge 24a, and the adapter seat 26 typically all have substantially the same outer and inner diameters so that they seat together with a good fit that prevents sample leakage during processing. To provide for good sealing, the flow disrupter 12, or at least its mounting flange 22, can be made of an elastomeric polymer, rubber, or another resiliently-deformable fluid-sealing material. In the depicted embodiment, the adapter 16 includes one internally flanged seat 26 and so the adapter has to be oriented with the flow disrupter 12 going in that end, but in other embodiments the adapter includes two seats facing away from each other and so the flow disrupter can go into either end of the adapter.

In other embodiments, the disrupter is secured in place on the adapter (e.g., with its mounting flange in a channel between two facing internally flanged seats) and thus not pinched against the container peripheral edge. In yet other embodiments, the disrupter is provided as an integral portion of the adapter, whether manufactured as a single piece or as two (or more) pieces and factory-assembled together. In still other embodiments, the flow disrupter is secured in place by screw threads that mate with screw threads of the adapter and/or the container, by an adhesive, by clamps, or by another conventional securement. And in other embodiments, the disrupter includes an axial extension element (e.g., a sleeve, cage, ribs, strips, and/or bars, either peripherally positioned, centrally positioned, or both), so that, with its mounting flange abutting the container peripheral edge, its flow-interrupting impact surfaces and flow-constricting passageway(s) are positioned axially deeper inside the tube-container chamber and farther away from the open-end peripheral edge, thereby permitting use with a conventional tube endcap and a conventional (or slightly radially oversized) size tube container to provide the functionality described herein.

In all of these embodiments, the flow disrupter is held securely in place relative to the tube assembly (defining the two adjacent sub-chambers with two constant volumes) so that the sample flow interruption is produced by the sample flowing relative to the fixed impact surfaces and flow passageway(s) in response to reciprocating shaking of the tube assembly, without the need for using any internal agitators, filters, tube pressurization, and/or other disruption structures/methods.

The flow disrupter 12 also includes a flow-interrupting body portion 28 extending generally transversely (e.g., radially) inward from the mounting flange 22 and dividing the internal space of the tube assembly 10 into two sub-chambers 32a and 32b (collectively, the sub-chambers 32). In typical embodiments, the sub-chambers 32 defined by the flow disrupter 12 are axially aligned (along the tube axis 33). The flow-interrupting body 28 can be in the form of a transversely inwardly extending flange (a disc or plate), as depicted. Or the flow-interrupting body can be in the form of one or a plurality of transversely extending arms, paddles, fins, or other structures.

In the depicted embodiment, for example, the disrupter 12 is positioned generally medially along the tube assembly 10 to form the sub-chambers 32 with substantially similar volumes. Typically, at least one of the sub-chambers 32 (a primary one) is sized with a volume large enough to hold the entire volume of the sample (both before and after processing for samples whose volume can be altered by homogenizing), though in other embodiments less than the entire sample but substantially all of it (e.g., about 90 percent, or about 95 percent of it) can be held in the primary sub-chamber 32 (or a larger-volume tube assembly can be used for a larger-volume sample). In other embodiments, a primary one of the sub-chambers 32a is sized to hold the sample to be homogenized and a head one of the sub-chambers 32b has a smaller volume that is a substantial portion (i.e., at least about 20 percent) of the total volume of the tube assembly 10 (the sub-chambers combined), and in some such embodiments the head sub-chamber is not necessary able to receive the entire sample volume (as noted above). In typical embodiments, the primary sub-chamber 32 has a volume of about 0.025 mL to about 50 mL, with these volumes noted for illustration purposes only and thus not limiting of the invention.

In addition, the flow-interrupting body 28 defines at least two flow-interrupting impact surfaces 29 and at least one flow-constricting passageway 30. Each flow-constricting passageway 30 provides a path for the sample to flow axially along the tube assembly 10 between the sub-chambers 32, and in this sense the flow passageway 30 is axial, though it does not need to be linear or even parallel to the sub-chamber axis 33. And each flow-constricting passageway 30 has a smaller inner diameter than the sub-chambers 32. In the depicted embodiment, the flow-interrupting body 28 includes a single axial flow passageway 30 in the form of an orifice that is cylindrical-shaped and positioned centrally in the flow-interrupting body (and thus along the centerline/axis 33 of the sub-chambers 32). As such, the sample flows through the flow passageway 30 between the sub-chambers 32 back-and-forth in a reciprocating manner, with the passageway constricting/throttling the sample flow as the sample passes through it in each axial direction.

In other embodiments, there are multiple flow-constricting passageways, and/or the flow-constricting passageway(s) are not centered, cylindrical, and/or parallel to the sub-chamber axis. In some such embodiments, the flow passageways have a shape that is helical, serpentine, zigzagged, angled, curved, or otherwise not parallel to the sub-chamber axis, while still providing for axial flow between the sub-chambers. In some such embodiments, the flow passageways have a cross-sectional shape that is not circular but instead is square, polygonal, star-shaped, or another regular or irregular shape. And in some such embodiments, the flow passageways can have a form other than an orifice, for example, they can be formed by empty space between knife-blade impact surfaces.

The size of the cross-sectional flow area of the flow passageway 30 (cumulative for multiple passageways) is selected based at least in part on the particle size and/or hardness of the sample to be homogenized as well as the cross-sectional flow area of the containers 14. That is, the cross-sectional flow area of the flow passageway 30 is typically larger for homogenizing samples with a larger particle size (e.g., a coronary artery segment or plant matter) and typically smaller for homogenizing samples with a smaller particle size (e.g., blood, yeast, or bacteria). And the cross-sectional flow area of the flow passageway 30 is always less than that of the sub-chambers 32 (e.g., each flow-constricting passageway has a smaller/reduced inner diameter relative to the sub-chambers). In typical representative embodiments, for example, the relative cross-sectional flow area of the flow passageway 30 is about ten percent to about ninety percent of the cross-sectional flow area of the containers 14.

The two or more flow-interrupting impact surfaces 29 of the flow-interrupting body 28 extend generally transversely (e.g., radially) across the internal chamber space of the containers 14, between the flow-disrupter mounting flange 22 and the flow-constricting passageway 30. At least two impact surfaces 29 are provided because the flow disrupter 12 is designed for homogenizing by a reciprocating shaking motion. So there are two generally oppositely arranged impact surfaces 29, on opposite sides of the flow-interrupting body 28, facing generally away from each other. In this way, regardless of which reciprocating direction the tube assembly 10 is traveling in, portions of the sample will impact one or the other of the two impact surfaces 29. In the depicted embodiment, there are two impact surfaces 29 of the same shape and size, one on each side of the flow-interrupting body 28. In other embodiments, there are multiple impact surfaces on one or both sides of the flow-interrupting body.

In the depicted embodiment, the impact surfaces 29, as well as the flow passageways formed by them, are substantially symmetrical in both axial directions (i.e., about a transverse plane). So as the sample flows back and forth between the two sub-chambers 32, it is subjected to substantially the same flow disruption in each axial direction. That is, the sample experiences similar disruption from impacting each of the two impacts surfaces and/or from flowing back-and-forth through the same flow passageway(s) in both axial directions (i.e., at least one flow passageway has two opposite and symmetrical conical portions for two-way throttling flow through it). In other embodiments, there are at least two flow passageways formed by the impact surfaces with each designed for one-way flow so that the sample is disrupted by flowing in a first axial direction through a first passageway and is then disrupted by flowing in a second opposite axial direction through a second passageway. And in other embodiments, the impact surface(s) on one side of the flow-interrupting body have a different shape and/or size from the impact surface(s) on the other side of the flow-interrupting body, for example with one designed for maximal homogenization by mechanical shear in one reciprocating axial direction and with the other designed for maximal homogenization by fluid shear in the other axial direction.

The transverse impact surfaces 29 of many embodiments, such as that depicted, include at least a portion that is perpendicular to the tube container axis 33 so that, when they are impacted by the sample, more of the kinetic energy of the sample tends to be used for homogenizing (given the generally axial flow of the sample). In the depicted embodiment, for example, each impact surface 29 includes an outer annular surface 36 that is flat and perpendicular, and an inner annular surface 34 that is flat and angled from perpendicular (e.g., ramped), with these two surface portions being continuous (e.g., no flow-through opening between them). The outer annular flat surfaces 36 provide for head-on collisions with the particles for good mechanical shearing of the sample particles. And the inner annular ramped surfaces 34 surround the flow passageway 30 and are wider at the outer annular flat surface 36 than at the flow passageway (i.e., with reducing geometry, e.g., a conical shape) to form a nozzle to create a throttling pressure differential and fluid shear stresses as sample particles are forced through the flow passageway. Thus, there are two oppositely arranged inner annular ramped surfaces 34, on opposite sides of the passageway 30, forming convergent and divergent nozzles in each reciprocating axial direction of sample flow.

In other embodiments, the transverse impact surfaces include only a perpendicular surface (flat or contoured) or only a ramped surface (flat or contoured). In yet other embodiments, the impact surfaces additionally or alternatively include other surfaces, for example knife-blade edge surfaces. And in still other embodiments, the impact surfaces (or portions of them) are curved, undulated, coarse, spiked, or otherwise have another regular or irregular surface.

The depicted flow-interrupting body 28 includes a cylindrical passageway surface 38 (defining the flow passageway 30), with the inner annular ramped surfaces 34 extending between the outer annular flat surfaces 36 and the cylindrical passageway surface. In other embodiments, the impact surfaces (e.g., the inner annular ramped surfaces) meet at an annular edge that defines the flow passageway.

Having described structural details of the tube assembly 10 and flow disrupter 12, details of their use will now be described with reference to FIGS. 5-7. As a preliminary step, a number of the tube assemblies 10 is selected based on the number of samples to be processed and the tube capacity of the homogenizer to be used. The tube assemblies are opened, the samples are inserted (e.g., into a primary container), and the tube assemblies are closed and mounted to the homogenizer. For illustration purposes, only one tube assembly will be referred to in this example.

The depicted homogenization is accomplished using a homogenizer device operable to axially reciprocatingly shake the tube assembly automatically at very high speeds, typically about 0.8 m/s to about 10.0 m/s for time periods of about 10 seconds to about 10.0 minutes, faster than can be accomplished by manual (i.e., hand) shaking for such time periods while maintaining controlled reliability (i.e., a substantially uniform amplitude and frequency of the reciprocal shaking for the full time period. Such homogenizers include drive motors and tube holders, and are referred to herein as "high-speed electro-mechanical homogenizers." Generally, through reciprocating shaking of the tube assembly 10 at such high velocities (as depicted by the directional arrows), the special flow-interrupting geometry of the flow disrupter 12 imparts forces on the sample that cause particle-size reduction as the sample moves back-and-forth between the two sub-chambers 32. As noted above, while the reciprocating action is referred to as axial, it is not necessarily purely linear and have be curved somewhat as depicted and as in common in swashing shaker-mill homogenizers. Of course, other conventional or modified homogenizers can be used that produce purely linear axial/reciprocating motion or that produce another reciprocating motion that is substantially axial but not purely linear, as noted herein. In addition, it should be noted that the generally axial travel (displacement) of the tube assembly 10 is substantially the same or longer than the axial length of the primary sub-chamber 32 in order to achieve optimal impacting of maximal portions of the sample against the impact surfaces 29, and in any event is typically at least half the length of the primary sub-chamber to longer than the full tube chamber.

In particular, as the tube assembly 10 is propelled at high speed in a first generally axial direction (see FIG. 5), portions of the sample forcefully impact the first-direction impact surface 29 such that mechanical shear forces cause break-up and/or disassociation of cells to achieve particle-size reduction. In addition, after this impaction, the same and/or other portions of the sample are forcefully accelerated then decelerated through the flow passageway 30 in the first axial direction resulting in significant pressure differentials, cavitation, and fluid shear stress causing further breakup and/or disassociation of cells to achieve further particle-size reduction.

Then as the tube assembly 10 is propelled at high speed in an opposite second generally axial direction (see FIG. 6), portions of the sample forcefully impact the second-direction impact surface 29 such that mechanical shear forces cause further break-up and/or disassociation of cells to achieve further particle-size reduction. In addition, after this impaction, the same and/or other portions of the partially-reduced sample are forcefully accelerated then decelerated back through the flow passageway 30 in the second axial direction resulting in significant pressure differentials, cavitation, and fluid shear stress causing further breakup and/or disassociation of cells to achieve further particle-size reduction.

Then the tube assembly 10 is propelled at high speed in the first generally axial direction again (see FIG. 7), then cycled back-and forth for a predetermined amount of time (or number of cycles) to complete the homogenizing. At the conclusion of the processing, the tube assembly 10 is opened and the sample is removed (e.g., poured or pipetted), without having to separate the sample from beads or anything else (other than the internal chamber surface of the tube assembly, of course). As such, more of the sample is recovered, and time and cost are saved, without sacrificing the effectiveness/quality of the homogenization, for a significant improvement in laboratory homogenization of samples.

In the depicted embodiment, the adapter 16 and the flow disrupter 12 are provided as two separate components. In other embodiments, the adapter and the disrupter are a unitary piece, with the disrupter formed as an integral component of the adapter and positioned for example between the two sets of female screw threads. And in yet other embodiments, the tube assembly includes two flow disrupters and is divided into three sub-chambers, with one positioned at each end of a modified version of the adapter that is elongated and includes two insert seats.

The flow disrupter can be provided with many variations for providing the functionality described herein. Some of these embodiments are shown in FIGS. 8-21, with each of these figures showing a flow disrupter in cross-section to show the internal structure and geometry. These flow disrupters are all substantially similar in fundamental design to that of the first embodiment described above, and for brevity only some major differences will be noted. It will be understood that any of the features of these flow disrupters, and/or others not described herein, can be combined to form additional flow-disrupter embodiments and tube assembly embodiments contemplated by and within the scope of the invention. As such, any of the flow disrupters of FIGS. 8-21 can be incorporated into any of the tube assemblies of FIGS. 1-2, 22-23, 24, 25, 26, 27, and so on.

It should be noted that the several embodiments of FIGS. 8-12 are believed to be highly effective in homogenizing, as they are variants of the single-orifice flow passageway embodiment described of FIGS. 1-7 that has been shown to be highly effective by testing. In addition, embodiments including multi-orifice flow passageways are believed to be capable of highly-effective homogenizing, especially in embodiments that include an array of sharpened edges peripherally about the flow passageways to "pre-process" tougher samples by mechanical shear forces before they accelerate then decelerate through the flow passageways.

FIGS. 8-10 show portions of flow disrupters 112, 212, and 312 according to second-fourth example embodiments of the invention. These flow disrupters 112, 212, and 312 are all similar to that of the first embodiment described above, for example they all include at least two oppositely-facing flow-interrupting impact surfaces 129, 229, and 329 and at least one flow-constricting passageway 130, 230, and 330. In these embodiments, however, the disrupters 112, 212, and 312 include multiple flow passageways 130, 230, and 320 and multiple ramped impact surfaces 134, 234, and 334 to provide additional flow disruption and particle-size reduction (e.g., via additional mechanical shear, fluid shear, and pressure differential).

In particular, the disrupter 112 of FIG. 8 includes four orifice-like flow passageways 130 with opposing impact surfaces 129 each having four conical ramped surfaces 134 positioned peripherally about the four flow passageways. The disrupter 212 of FIG. 9 includes ten orifice-like flow passageways 230 with opposing impact surfaces 229 each having ten conical ramped surfaces 234 positioned peripherally about the ten flow passageways. And the disrupter 212 of FIG. 10 includes nineteen orifice-like flow passageways 230 with opposing impact surfaces 229 each having nineteen conical ramped surfaces 234 positioned peripherally about the nineteen flow passageways. In addition, the mounting flanges and the flow-interrupting bodies of the flow disrupters 112 and 312 have the same axial thickness, and the mounting flange of the flow disrupter 212 has a larger axial thickness than its flow-interrupting body.

FIG. 11 shows a portion a of flow disrupter 412 according to a fifth example embodiment of the invention. This flow disrupter 412 is similar to that of the first embodiment described above, for example it includes at least two oppositely-facing flow-interrupting impact surfaces 429 and at least one flow-constricting passageway 430. In this embodiment, however, the disrupter 412 includes seven orifice-like flow passageways 430 to provide additional flow disruption and particle-size reduction (e.g., via additional mechanical shear, fluid shear, and pressure differential). In addition, the two opposing impact surfaces 429 do not include any ramped surfaces for throttling, and the mounting flange and the flow-interrupting body of the flow disrupter 412 have the same axial thickness.

Figure 12:
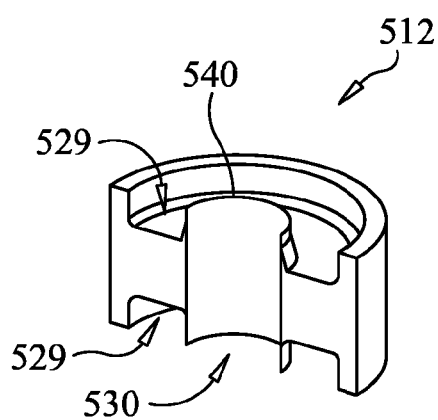
FIG. 12 is a cross-sectional perspective view a flow disrupter according to a sixth example embodiment of the invention.

FIG. 12 shows a portion of a flow disrupter 512 according to a sixth example embodiment of the invention. This flow disrupter 512 is similar to that of the first embodiment described above, for example it includes at least two oppositely-facing flow-interrupting impact surfaces 529 and at least one flow-constricting passageway 530. More particularly, the disrupter 512 includes a single, center, relatively-large-diameter orifice-like flow passageway 530. In this embodiment, however, the impact surfaces 529 include two narrow-tipped (e.g., sharp-tipped) flanged annular fins 540 surrounding the orifice passageways 530 and extending in opposite axial directions from each other (form each side of the disrupter body) to provide additional flow disruption and particle-size reduction (e.g., via additional mechanical shear). In addition, the impact surfaces 529 do not include any throttling ramped surfaces adjacent the flow passageway 530, and the mounting flange of the flow disrupter 512 has a larger axial thickness than its flow-interrupting body.

Figure 13:
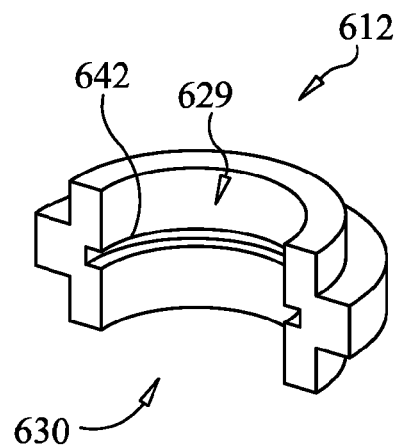
FIG. 13 is a cross-sectional perspective view a flow disrupter according to a seventh example embodiment of the invention.

FIG. 13 shows a portion of a flow disrupter 612 according to a seventh example embodiment of the invention. This flow disrupter 612 is similar to that of the first embodiment described above, for example it includes at least two oppositely-facing flow-interrupting impact surfaces 629 and at least one flow-constricting passageway 630. More particularly, the disrupter 612 includes a single, center, relatively-large-diameter orifice-like flow passageway 630. In this embodiment, however, the impact surfaces 629 do not include the throttling ramped surfaces, but the disrupter 612 includes a larger-diameter passageway 630 and additionally includes an annular groove 642 with an open side facing radially inward, to provide additional flow disruption and particle-size reduction (e.g., via additional mechanical shear).

FIGS. 14-21 show additional example embodiments in which the flow disrupters are similar to those described above but with some differences. In particular, in these embodiments the flow-interrupting body includes at least one transverse fin with at least one ramped surface that at least partially defines at least one of the impact surfaces. Of course, these embodiments are just a few of the many contemplated by the invention, and additional embodiments include flow disrupters with other numbers, shapes, and/or arrangements of transverse fins defining ramped/impact surfaces.

Figure 14:
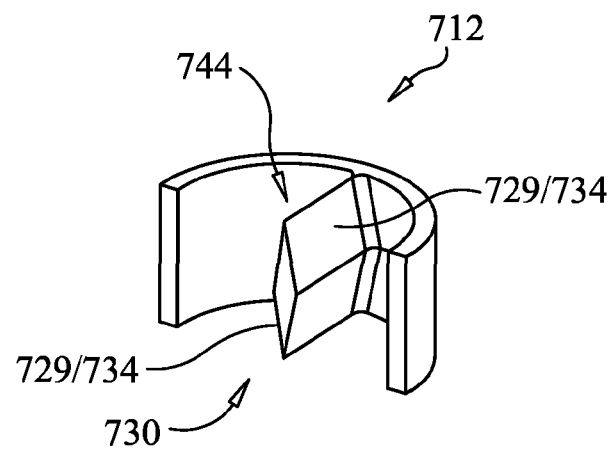
FIG. 14 is a cross-sectional perspective view a flow disrupter according to an eighth example embodiment of the invention.

FIG. 14 shows a portion of a flow disrupter 712 according to an eighth example embodiment of the invention. This flow disrupter 712 is similar to that of the first embodiment described above, for example it includes at least two oppositely-facing flow-interrupting impact surfaces 729 and at least one flow-constricting passageway 730. In this embodiment, however, the flow-interrupting body includes a transverse (e.g., radial) fin 744 defining the impact surfaces 729 as four ramped surfaces 734 (without any perpendicular surfaces), with two ramped surfaces facing in one general axial direction (sufficiently for throttling, not oriented facing truly axially) and the other two facing generally oppositely, with each pair of ramped surfaces extending axially away from the other pair, and with each pair of ramped surfaces forming a narrow (e.g., sharp) tip, to provide additional flow disruption and particle-size reduction (e.g., via additional mechanical shear). In addition, the disrupter 712 includes two flow passageways 730 formed by the two void spaces (e.g., semi-circular) between the transverse fin 744 and the inner surface of the disrupter (i.e., of the mounting flange and/or the flow-interrupting body) that the fin extends from. Also, the mounting flange and the flow-interrupting body of the flow disrupter 712 have the same axial thickness.

Figure 15:
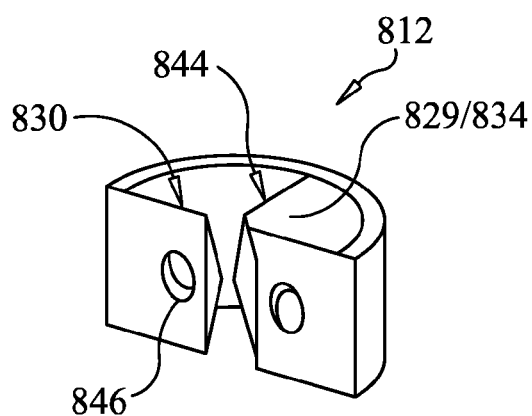
FIG. 15 is a cross-sectional perspective view a flow disrupter according to a ninth example embodiment of the invention.

FIG. 15 shows a portion of a flow disrupter 812 according to a ninth example embodiment of the invention. This flow disrupter 812 is similar to that of the eighth embodiment described immediately above, for example its flow-interrupting body includes a transverse (e.g., radial) fin 844 defining the impact surfaces 829 as ramped surfaces 834 (without any perpendicular surfaces), with pairs of the ramped surfaces forming a narrow (e.g., sharp) tip, and with at least two pairs of the ramped surfaces extending axially away from the other. In this embodiment, however, the flow-interrupting body includes two intersecting transverse fins 844 in an X-shaped (e.g., perpendicularly crossed) arrangement, with the resulting four spokes of the transverse fins 844 defining the impact surfaces 829 as eight ramped surfaces 834, with four ramped surfaces facing in one general axial direction (sufficiently for throttling, not oriented facing truly axially) and the other four facing generally oppositely, with the resulting four void spaces defining four flow passageways 830, to provide additional flow disruption and particle-size reduction (e.g., via additional mechanical shear). Also, openings 846 such as sharp-edged through-holes can be formed in the fins 844 to provide additional flow disruption (e.g., via additional mechanical shear), for example with the holes angled to induce a helical flow to provide additional flow disruption (e.g., via additional fluid shear). In addition, the mounting flange and the flow-interrupting body of the flow disrupter 812 have the same axial thickness.

Figure 16:
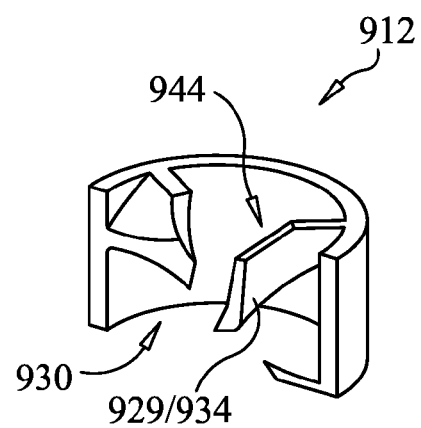
FIG. 16 is a cross-sectional perspective view a flow disrupter according to a tenth example embodiment of the invention.

FIG. 16 shows a portion of a flow disrupter 912 according to a tenth example embodiment of the invention. This flow disrupter 912 is similar to that of the eighth and ninth embodiments described immediately above, for example its flow-interrupting body includes transverse (e.g., radial) fins 944 defining the impact surfaces 929 as ramped surfaces 934 (without any perpendicular surfaces). In this embodiment, however, three fins 944 (only two can be seen in this view) each define two opposing ramped impact surfaces 929/934 that are helical (i.e., six total, with three impact surfaces generally facing each axial direction), with the three void spaces between the three fins defining three helical flow passageways 930, with the fin ramped surfaces including narrow (e.g., sharp) tips, to induce a helical flow in either axial reciprocating sample-flow direction, to thus provide additional flow disruption and particle-size reduction (e.g., via additional mechanical shear, fluid shear, and pressure differential). In addition, and the mounting flange and the flow-interrupting body of the flow disrupter 912 have the same axial thickness. In some embodiments, the fins have a non-constant thickness such that the ramped impact surfaces produce a convergent/divergent throttling action in both axial flow directions.

Figure 17:
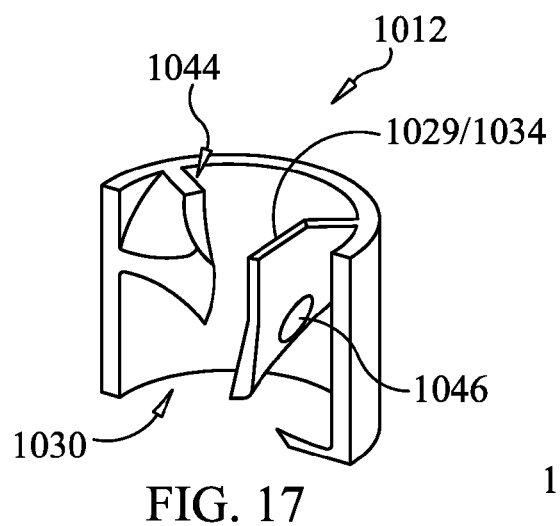
FIG. 17 is a cross-sectional perspective view a flow disrupter according to an eleventh example embodiment of the invention.

FIG. 17 shows a portion of a flow disrupter 1012 according to an eleventh example embodiment of the invention. This flow disrupter 1012 is similar to that of the tenth embodiment described immediately above, for example it includes three transverse fins 1044 (only two can be seen in this view) each defining two opposing helical ramped impact surfaces 1029/1034 (i.e., six total, with three impact surfaces generally facing each axial direction), with the three void spaces between the three fins defining three helical flow passageways 1030, with the fin ramped surfaces including narrow (e.g., sharp) tips, to induce a helical flow in either axial reciprocating sample-flow direction. In this embodiment, however, the disrupter 1012 additionally includes openings 1046 such as sharp-edged holes (ala those of FIG. 15) in the fins 1044 to provide additional flow disruption and particle-size reduction (e.g., via mechanical shear), for example with the holes angled to induce a helical flow to provide additional flow disruption (e.g., via fluid shear).

Figure 18:
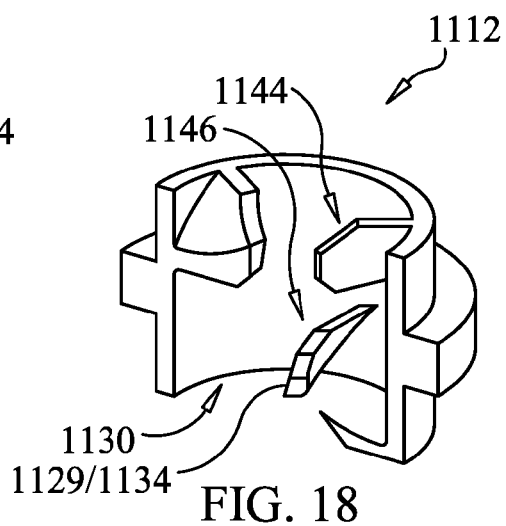
FIG. 18 is a cross-sectional perspective view a flow disrupter according to a twelfth example embodiment of the invention.

FIG. 18 shows a portion of a flow disrupter 1112 according to a twelfth example embodiment of the invention. This flow disrupter 1112 is similar to that of the eleventh embodiment described immediately above, for example it includes three transverse fins 1144 (only two can be seen in this view) each defining two opposing helical ramped impact surfaces 1129/1134 (i.e., six total, with three impact surfaces generally facing each axial direction), with the three void spaces between the three fins defining three helical flow passageways 1130, to induce a helical flow in either axial reciprocating sample-flow direction. In this embodiment, however, the fins 1144 include openings 1146 in the form of sharp-edged transverse slots to provide additional flow disruption and particle-size reduction (e.g., via additional mechanical shear). In some embodiments, the slots define edges that are not helically aligned (adjacent edges are alternatingly angled inward and outward in a propeller-like arrangement) and/or the slots are coextensive with the fins thereby forming multiple fins that are axially spaced but not helically aligned (not smooth if continuous), for added flow disruption and particle-size reduction.

Figure 19:
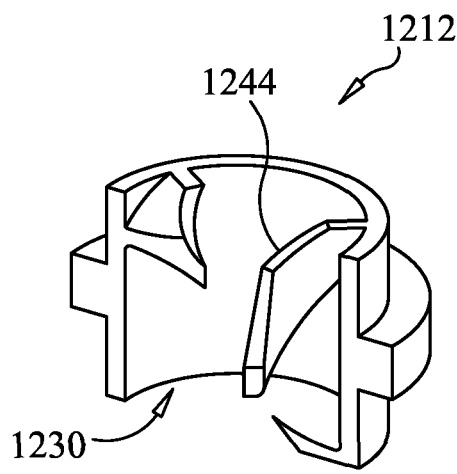
FIG. 19 is a cross-sectional perspective view a flow disrupter according to a thirteenth example embodiment of the invention.
Figure 20:
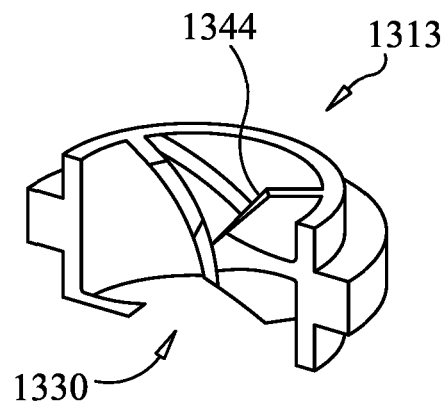
FIG. 20 is a cross-sectional perspective view a flow disrupter according to a fourteenth example embodiment of the invention.
Figure 21:
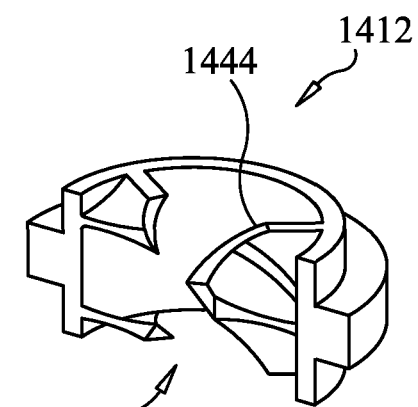
FIG. 21 is a cross-sectional perspective view a flow disrupter according to a fifteenth example embodiment of the invention.

FIGS. 19-21 show flow disrupters 1212, 1312, and 1412 according to thirteenth through fifteenth example embodiments of the invention. These flow disrupters 1212, 1312, and 1412 are similar to the helical-finned embodiment of FIG. 16, with a few minor exceptions. In particular, the disrupter 1212 of FIG. 19 includes helical fins 1244 that are axially more elongated to thus form relatively axially-longer flow passageways 1230 (and that in this particular embodiment have a shallower pitch), the disrupter 1312 of FIG. 20 includes helical fins 1344 that have an opposite-hand angular orientation to thus form helically-opposite flow passageways 1330, and the disrupter 1412 of FIG. 21 includes flow passageways 1430 formed by helical fins 1444 having an increased wall thickness for improved strength.

FIGS. 22-27 show various improved sample tube assemblies according to additional example embodiments of the present invention. The tube assemblies and flow disrupters of these embodiments are substantially similar to those of the embodiments described above, with some differences of note described. These tube assemblies can include any of the flow disrupters described herein, and the specific flow-disrupting features of the depicted flow-disrupter embodiments are for illustration purposes only.

The use, function, and result produced by the tube assemblies and flow disrupters of these embodiments are substantially similar to that of the first embodiment described above. That is, the special structure and geometry of the flow disrupter disrupts the flow of the sample within the tube chamber during processing as the sample is forced between the sub-chambers to significantly reduce particle size of the sample without using grinding beads or other media.

Figure 22:
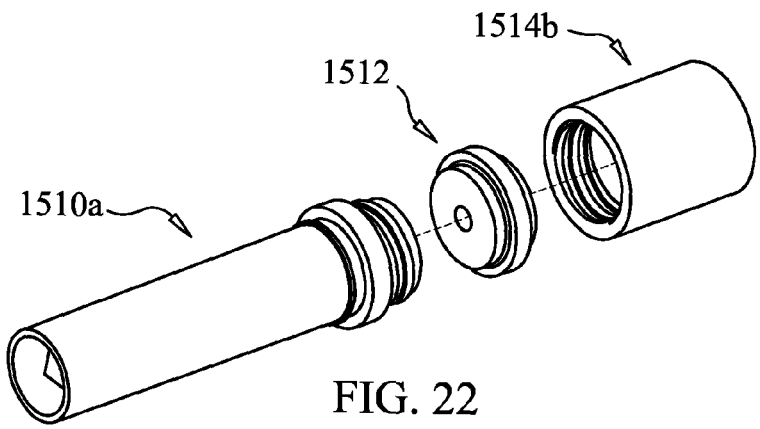
FIG. 22 is an exploded perspective view of a sample tube assembly with a flow disrupter according to a sixteenth example embodiment of the invention.
Figure 23:
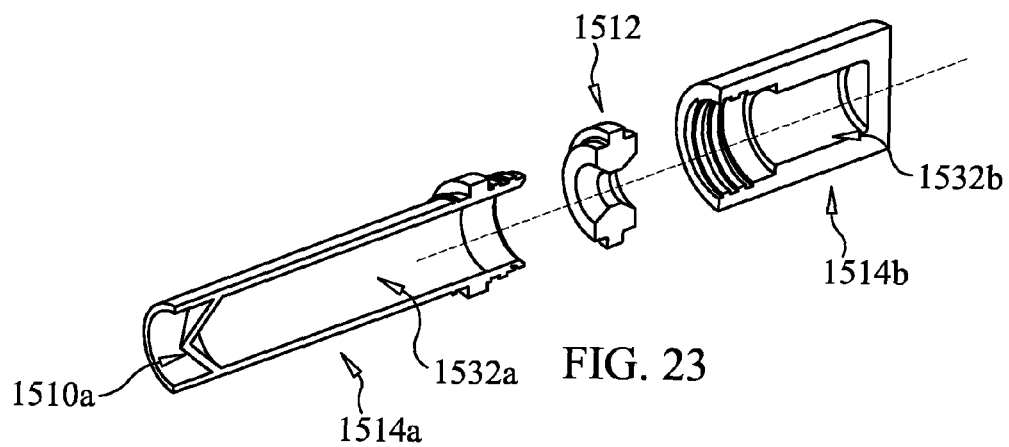
FIG. 23 is a longitudinal cross-section view of the tube assembly with the flow disrupter of FIG. 22.

FIGS. 22-23 show an improved sample tube assembly 1510 according to a sixteenth example embodiment of the present invention. The sample tube assembly 1510 includes a flow disrupter 1512 and two container shell components, one being a first container 1514a forming a first sub-chamber 1532a of the same type as provided by the first embodiment described above. Of course, first containers and flow disrupters of many other embodiments can be provided instead, for example those including features of any of the embodiments described herein.

In this embodiment, however, a different second container shell component forming a modified second sub-chamber 1532b is provided. In particular, the second container 1514b is in the form of a conventional endcap commonly used with the first container 1514a, except modified to be axially longer to form the second sub-chamber 1532b. As such, the first (primary) sub-chamber 1532a is typically larger than the second (head) sub-chamber 1532b, and the sample is initially placed into the larger first/primary sub-chamber before processing. Also, the second container 1514b removably mounts directly to the first container 1514a, so an adapter is not needed.

Figure 24:
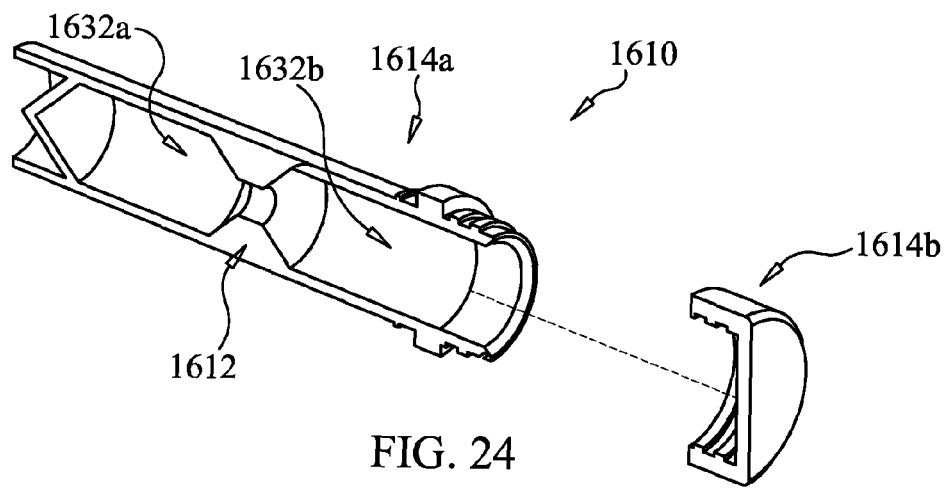
FIG. 24 is an exploded perspective longitudinal cross-section view of a sample tube assembly with a flow disrupter according to a seventeenth example embodiment of the invention.

FIG. 24 shows an improved sample tube assembly 1610 according to a seventeenth example embodiment of the present invention. The tube assembly 1610 includes a flow disrupter 1612 and two container shell components, one being a first container 1614a of a similar type as provided by the first embodiment described above. Of course, first containers and flow disrupters of many other embodiments can be provided instead, for example those including features of any of the embodiments described herein. In this embodiment, however, the first container 1614a and the flow disrupter 1612 are integrally formed as a unitary piece, with these components thus not including any cooperating mounting features for the flow disrupter. In addition, the flow disrupter is positioned at an intermediate portion of the container 1614a, not at its end, to form the first and second sub-chambers 1632a and 1632b in the first container. Furthermore, a different second container shell component can be provided, such as the depicted conventional endcap 1614b (of a conventional tube assembly).

Figure 25:
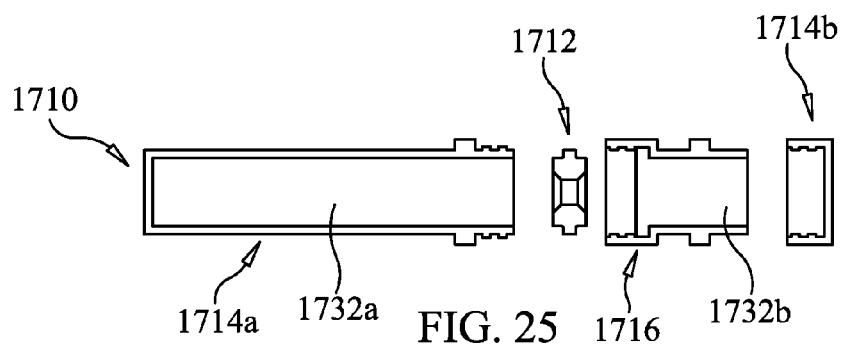
FIG. 25 is an exploded longitudinal cross-section view of a sample tube assembly with an adapter and a flow disrupter according to an eighteenth example embodiment of the invention.

FIG. 25 shows an improved sample tube assembly 1710 according to an eighteenth example embodiment of the present invention. The sample tube assembly 1710 includes a flow disrupter 1712 (e.g., of the same or a similar type as in FIGS. 1-4), a first container shell component 1714a forming the first sub-chamber 1732a (e.g., a container of the same or a similar type as in FIGS. 1-4), a second container shell component 1714b (e.g., an endcap of the same or a similar type as in FIG. 24), and an adapter 1716 for removably coupling the container shell parts together and including female/internal screw threads for removably coupling to the first container. Of course, container shell components and flow disrupters of many other embodiments can be provided instead, for example those including features of any of the embodiments described herein. In this embodiment, however, the adapter 1716 includes male/external screw threads at its other end for removably coupling to the female/internal screw threads of the endcap 1714b. And the adapter 1716 is axially elongated so that it at least partially forms the second sub-chamber 1732b.

Figure 26:
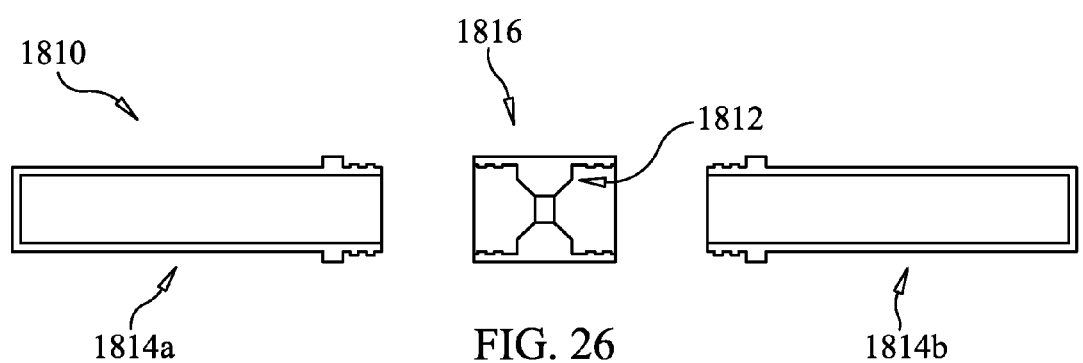
FIG. 26 is an exploded longitudinal cross-section view of a sample tube assembly with an adapter and a flow disrupter according to a nineteenth example embodiment of the invention.

FIG. 26 shows an improved sample tube assembly 1810 according to a nineteenth example embodiment of the present invention. The sample tube assembly 1810 includes an integral flow disrupter 1812 (e.g., of the same or a similar type as in FIG. 24), first and second container shell components 1814a and 1814b (e.g., containers of the same or a similar type as in FIGS. 1-4), and an adapter 1816 for removably coupling the container shell parts together. Of course, container shell components and flow disrupters of many other embodiments can be provided instead, for example those including features of any of the embodiments described herein. In this embodiment, however, the adapter 1816 and the flow disrupter 1812 are integrally formed as a unitary piece, with these components thus not including any cooperating mounting features for the flow disrupter.

Figure 27:
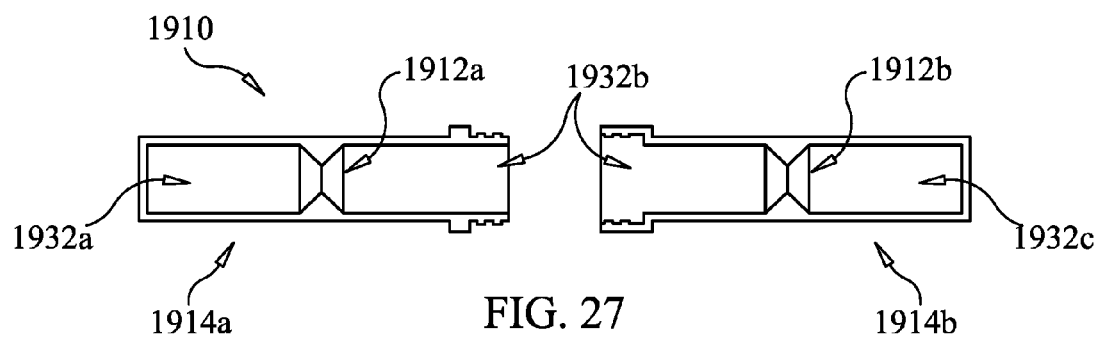
FIG. 27 is an exploded longitudinal cross-section view of a sample tube assembly with two flow disrupters according to a twentieth example embodiment of the invention.

FIG. 27 shows an improved sample tube assembly 1910 according to a twentieth example embodiment of the present invention. The sample tube assembly 1910 includes a first container shell component 1914a and an integral first flow disrupter 1912a (e.g., of the same or a similar types as in FIG. 24). Of course, container shell components and flow disrupters of many other embodiments can be provided instead, for example those including features of any of the embodiments described herein. In this embodiment, however, the sample tube assembly 1910 includes a second container shell component 1914b and an integral second flow disrupter 1912b (e.g., of the same or a similar types as in FIG. 24, except for including mating screw threads as depicted or alternatively including an adapter). As such, this embodiment includes two axially spaced flow disrupters 1912a and 1912b that divide the tube chamber into three axially aligned sub-chambers 1932a, 1932b, and 1932c.

Figure 28:
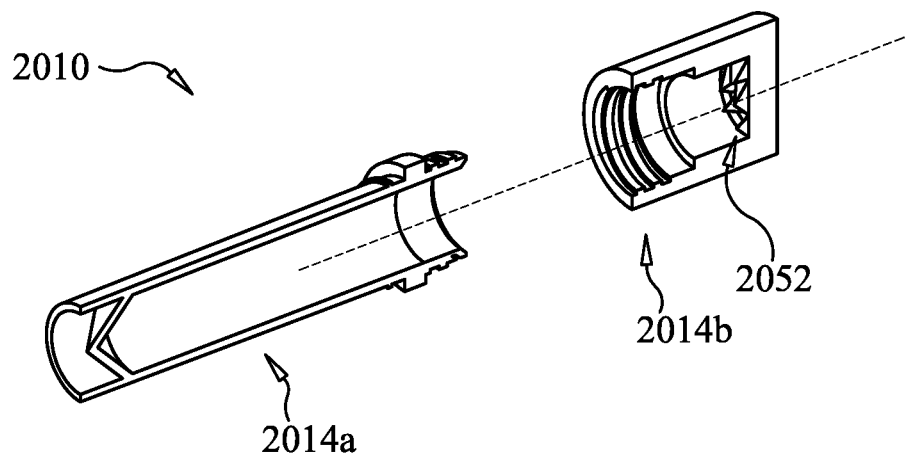
FIG. 28 is an exploded perspective longitudinal cross-section view of a sample tube assembly with an integral end-wall flow disrupter according to a twenty-first example embodiment of the invention.
Figure 29:
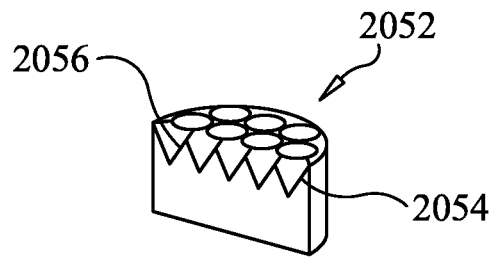
FIG. 29 is a cross-sectional perspective view of an insert embodiment of the end-wall flow disrupter of FIG. 28.
Figure 30:
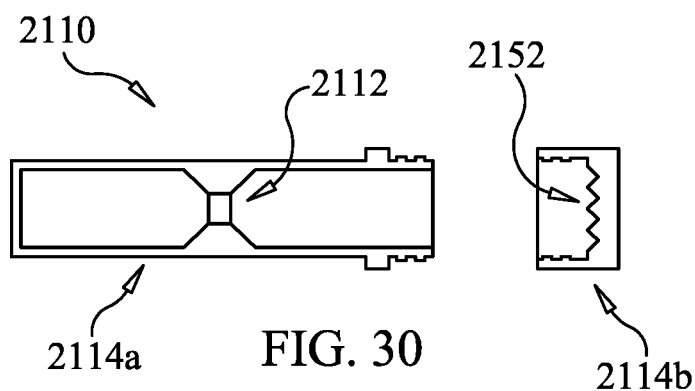
FIG. 30 is an exploded longitudinal cross-section view of a sample tube assembly with a flow-through flow disrupter and an end-wall flow disrupter according to a twenty-second example embodiment of the invention.

FIGS. 28-30 show various improved sample tube assemblies according to additional example embodiments of the present invention. The tube assemblies and flow disrupters of these embodiments share similarities to those of the embodiments described above, with some major differences noted.

FIGS. 28-29 show an improved sample tube assembly 2010 according to a twenty-first example embodiment of the present invention. The sample tube assembly 2010 includes a first container shell component 2014a (e.g., a container of the same or a similar type as in FIGS. 1-4), with a modified second container shell component 2014b and flow disrupter 2052. In this embodiment, the flow disrupter 2052 does not divide the first and second container shell components 2014a and 2014b into sub-chambers (so there is only a single processing chamber), and does not include any flow passageways through which the sample flows. Instead, the flow disrupter 2052 is an inner endwall surface of the first and/or second containers 2014a and 2014b. For example, the flow disrupter 2052 can be formed as an integral inner endwall surface of a second container shell component in the form of an otherwise conventional endcap 2014b, as shown in FIG. 28. Or the flow disrupter 2052 can be formed as an insert that attaches to the first and/or second container shell components 2014a and/or 2014b, as shown in FIG. 29. Other than the inclusion of the flow disrupter 2052, the first and second container shell components 2014a and 2014b can be provided by conventional tube containers and endcaps.

The flow disrupter surface 2052 includes flow-interrupting structures and geometry that reduce particle size when reciprocatingly shaking the sealed tube assembly 2010 generally axially at high velocities to cause the sample to impact against the specialized flow-interrupting structures, without using grinding beads or other media. In the depicted embodiment, for example, the specialized flow-interrupting structures and geometry include an array of conical recesses 2054 in the surface of the flow disrupter 2052 forming sharp bottom and top edges 2056 for flow disruption causing particle-size reduction (e.g., by mechanical shear and fluid shear, and in some designs by pressure differentials).

FIG. 30 shows an improved sample tube assembly 2110 according to a twenty-second example embodiment of the present invention. The sample tube assembly 2110 includes a first container shell component 2114*a* and a first flow disrupter 2112 (e.g., a container and integral flow disrupter of the same or a similar type as in FIG. 24). And the sample tube assembly 2110 also includes a second container shell component 2114*b* and a second flow disrupter 2152 (e.g., an endcap and integral flow disrupter of the same or a similar type as in FIG. 28). As such, this embodiment combines the flow-through disruption of the embodiments of FIGS. 1-27 with the endwall disruption of the embodiments of FIGS. 28-29.

The improved tube assemblies and/or flow disrupters disclosed herein can be used with conventional high-powered shaker-mill homogenizer devices or other sample-agitation devices that generate generally axial forces (not necessarily truly linearly axial reciprocating motions and forces). Such homogenizer devices can include for example that disclosed by U.S. Provisional Patent Application Ser. No. 62/072,655, filed Oct. 30, 2014, and titled "RECIPROCATING TUBE-SHAKING MECHANISMS FOR PROCESSING A MATERIAL," which discloses a typical swashing motion that generates such generally axial but not truly linear reciprocating forces. In some homogenizing applications, the tube assemblies and/or flow disrupters disclosed herein can be used without shaker-mill homogenizers and instead can be shaken by hand.

Additional embodiments of the invention are not expressly disclosed herein but will be understood by persons of ordinary skill in the art to be within the scope of the invention. For example, the specific features of each embodiment described herein, and obvious design variations thereof, can be combined into any new combination, alone and/or with additional features not disclosed herein, to form additional embodiments. As such, another embodiment includes the embodiment of FIGS. 22-23 with the flow disrupter integrally formed in the endcap. And yet another embodiment includes the embodiment of FIGS. 22-23 with the endcap having a larger diameter for a larger sub-chamber volume (i.e., forming a generally T-shaped tube assembly).

In addition, in other embodiments the flow disrupter body is formed longitudinally along substantially the entire length of the inner surface of the peripheral wall(s) of the tube shell component(s), without dividing the tube chamber into two sub-chambers. And in other embodiments, the flow disrupter body is formed longitudinally along only a portion of the entire length of the inner surface of the peripheral wall(s) of the tube shell component(s), while still dividing the tube chamber into two sub-chambers, with these embodiments being essentially the same as the depicted flow-through disruptors, only longer. In such embodiments, the flow disrupter can be an addition to or a substitute for a flow-through disrupter and/or an end-wall disrupter, and it can be in the general form of any of the embodiments described and shown herein, only longer. In some such embodiments, the transverse impact surfaces include only a perpendicular surface (flat or contoured) or only a ramped surface (flat or contoured). In yet other such embodiments, the impact surfaces additionally or alternatively include other surfaces, for example knife-blade edge surfaces. And in still other such embodiments, the impact surfaces (or portions of them) are curved, undulated, coarse, spiked, or otherwise have another regular or irregular surface.

Furthermore, in additional embodiments the flow disrupter does not include the impact surfaces and its flow passageway(s) are not narrower than the sub-chambers for flow constriction/throttling. Instead, the flow passageway(s) are equal to or wider than the sub-chambers in cross-sectional flow area for flow disruption by alternative pressure differentials and fluid shear.

In another aspect, the invention includes methods of homogenizing samples using high-speed homogenizers, tube assemblies, and flow disrupters, without any grinding media, according to the herein-disclosed methods for using these items.

It is to be understood that this invention is not limited to the specific devices, methods, conditions, or parameters described and/or shown herein, and that the terminology used herein is for the purpose of describing particular embodiments by way of example only. Thus, the terminology used herein is intended to be broadly construed and is not intended to be unnecessarily limiting of the claimed invention. For example, as used in the specification including the appended claims, the singular forms "a," "an," and "one" include the plural, the term "or" means "and/or," and reference to a particular numerical value includes at least that particular value, unless the context clearly dictates otherwise. In addition, any methods described herein are not intended to be limited to the sequence of steps described but can be carried out in other sequences, unless expressly stated otherwise herein.

While the invention has been shown and described in exemplary forms, it will be apparent to those skilled in the art that many modifications, additions, and deletions can be made therein without departing from the spirit and scope of the invention as defined by the following claims.

What is claimed is:

1. A laboratory homogenizer tube assembly that mounts to a laboratory homogenizer for homogenizing a sample by axially-reciprocal shaking, the tube assembly comprising:
   two shell components that removably couple together to form an internal tube chamber with a longitudinal axis,
   a flow disrupter including a flow-interrupting body that extends generally transversely to the tube-chamber axis and into the tube chamber to divide the tube chamber into two axially-aligned sub-chambers, the body including at least two flow-interrupting impact surfaces and at least one flow-constricting passageway,
   wherein the at least one flow-constricting passageway is defined at least in part by and extends between the two flow-interrupting impact surfaces, has a cross-sectional flow area that is less than a cross-sectional flow area of the two sub-chambers, and forms a path for the sample to flow generally axially between the two sub-chambers in an accelerating then decelerating sequence in response to the axially-reciprocal shaking of the tube assembly, and
   wherein the at least two flow-interrupting impact surfaces are generally oppositely arranged on the flow-interrupting body facing in generally opposite axial directions, and wherein the two shell components cooperate with the two flow-interrupting impact surfaces to define the two sub-chambers, so that a first one of the impact surfaces is impacted by the sample as the sample flows in a first axial direction in a first one of the sub-chambers toward a second one of the sub-chambers, and a second one of the impact surfaces is impacted by the sample as the sample flows in a second axial direction in the second sub-chamber back toward the first sub-chamber during the axially-reciprocal shaking of the tube assembly.

2. The laboratory homogenizer tube assembly of claim 1, wherein:
the sample impacting against the impact surfaces and flowing through the flow-constricting passageway produces particle-size reduction of the sample by mechanical shear stress, pressure differentials, fluid shear stress, or cavitation, or a combination thereof, without a need to use grinding media in the tube chamber,
the homogenizer produces the axially-reciprocal shaking of the tube assembly at higher speeds, for longer time periods, or with more-uniform controlled reliability, or a combination thereof, than by hand-shaking,
the flow-constricting passageway is generally axially oriented within the tube chamber, the impact surfaces are impacted by the sample before the flow-constricting passageway receives the sample during the axially-reciprocal shaking of the tube assembly, or
a total volume of the tube chamber includes a first volume of a first one of the sub-chambers defined by the flow disrupter and a second volume of a second one of the sub-chambers defined by the flow disrupter, and wherein the second sub-chamber volume is at least about 20 percent of the chamber total volume.

3. The laboratory homogenizer assembly of claim 1, wherein the two shell components include a conventional tube container and a modified tube endcap.

4. The laboratory homogenizer tube assembly of claim 3, wherein the conventional tube container at least partially forms a first one of the two axially-aligned sub-chambers and the modified tube endcap at least partially forms a second one of the two axially-aligned sub-chambers.

5. The laboratory homogenizer tube assembly of claim 3, wherein the modified tube endcap is elongated along the longitudinal axis of the tube chamber relative to a conventional tube endcap.

6. The laboratory homogenizer tube assembly of claim 3, wherein the conventional tube container includes a tube coupling element and the modified tube endcap includes an endcap coupling element that connects to tube coupling element.

7. The laboratory homogenizer tube assembly of claim 6, wherein the tube coupling element and the endcap coupling element each include mating screw threads.

8. The laboratory homogenizer tube assembly of claim 1:
further comprising an adapter that removably couples together the two shell components;
wherein the adapter removably secures the flow disrupter in place, or wherein the adapter and the flow disrupter are integrally formed as a unitary part;
wherein the two shell components include two conventional tube containers, or wherein the two shell components include a conventional tube container and a conventional tube endcap;
further comprising a second flow disrupter formed by or positioned on an endwall inner surface of the tube chamber; or
wherein the flow disrupter is integrally formed as a unitary part of the tube assembly.

9. The laboratory homogenizer tube assembly of claim 1, wherein the flow disrupter includes a mounting structure adapted for mounting the flow-interrupting body of the flow-disrupter within the tube chamber.

10. The laboratory homogenizer tube assembly of claim 9, wherein the mounting structure of the flow disrupter includes a mounting flange that extends radially outwardly from the flow-interrupting body.

11. The laboratory homogenizer tube assembly of claim 1, wherein the flow-constricting passageway of the flow disrupter is generally axially oriented along the longitudinal axis of the tube chamber.

12. The laboratory homogenizer tube assembly of claim 1, wherein the impact surfaces of the flow disrupter are impacted by the sample before the flow-constricting passageway receives the sample during the axially-reciprocal shaking of the tube assembly.

13. The laboratory homogenizer tube assembly of claim 1, wherein at least one of the flow-interrupting surfaces of the flow disrupter includes at least one generally perpendicular surface portion, and wherein at least one of the flow-interrupting surfaces of the flow disrupter includes at least one ramped surface portion that is generally conically shaped, that is concentric to and surrounded by the generally perpendicular surface portion, and that is concentric to and surrounds the flow passageway.

14. The laboratory homogenizer tube assembly of claim 1, wherein at least one of the flow-interrupting surfaces of the flow disrupter includes at least one generally perpendicular surface portion, and wherein:
at least one of the flow-interrupting surfaces of the flow disrupter includes at least one axially-extending annular fin surrounding the flow passageway and extending axially from the generally perpendicular surface portion; or
the at least one flow-constricting passageway through the flow-interrupting body comprises a plurality of flow-constricting passageways formed through the flow-interrupting body, each of the flow-constricting passageways oriented parallel to the longitudinal axis of the tube chamber and defined in part by a ramped surface portion that is generally conically shaped, surrounding the respective flow passageway, at least partially surrounded by the generally perpendicular surface portion, and forms at least one of the flow-interrupting surfaces.

15. The laboratory homogenizer tube assembly of claim 1, wherein at least one of the flow-interrupting surfaces of the flow disrupter includes at least one ramped surface portion that is generally helically shaped and formed by a transverse fin of the flow-interrupting body;
wherein the flow-interrupting body of the flow disrupter includes at least one fin having a transverse flow opening formed therein; or
wherein the flow-interrupting body of the flow disrupter includes at least one annular groove with an open side facing inward.

16. A laboratory homogenizer tube assembly that mounts to a laboratory homogenizer for homogenizing a sample by axially-reciprocal shaking, the tube assembly comprising:
two shell components that removably couple together to form an internal tube chamber with a longitudinal axis, wherein the two shell components include a conventional laboratory homogenizer tube container and a modified laboratory homogenizer tube endcap, wherein the conventional tube container includes a tube coupling element and the modified tube endcap includes an endcap coupling element that connects to tube coupling element, wherein the tube coupling element and the endcap coupling element each include mating screw threads, wherein the tube container includes an open end into which the sample is inserted into the tube chamber for homogenizing use and out of which the homogenized sample is removed from the tube chamber after use, and wherein the modified tube endcap is modified by being elongated along the longitudinal axis of the tube chamber relative to a conventional tube endcap; and a flow disrupter secured in place against movement within the tube chamber, the flow disrupter including a flow-interrupting body that extends generally transversely to the tube-chamber axis and into the tube chamber to divide the tube chamber into two axially-aligned sub-chambers, the flow-interrupting body including at least two flow-interrupting impact surfaces and at least one flow-constricting passageway, wherein a first one of the two axially-aligned sub-chambers is at least partially formed by the conventional tube container and wherein a second one of the two axially-aligned sub-chambers is at least partially formed by the modified tube endcap, wherein the flow disrupter further includes a mounting structure adapted for mounting the flow-interrupting body within the tube chamber, wherein the mounting structure includes a mounting flange that extends radially outwardly from the flow-interrupting body, wherein the at least one flow-constricting passageway is defined at least in part by and extends between the two flow-interrupting impact surfaces, has a cross-sectional flow area that is less than a cross-sectional flow area of the two sub-chambers, and forms a path for the sample to flow generally axially between the two sub-chambers in an accelerating then decelerating sequence in response to the axially-reciprocal shaking of the tube assembly, wherein the at least two flow-interrupting impact surfaces are generally oppositely arranged on the flow-interrupting body facing in generally opposite axial directions, and wherein the two oppositely-arranged flow-interrupting impact services of the flow disrupter each partially define a respective one of the two sub-chambers, so that a first one of the impact surfaces is impacted by the sample as the sample flows in a first axial direction in a first one of the sub-chambers toward a second one of the sub-chambers, and a second one of the impact surfaces is impacted by the sample as the sample flows in a second axial direction in the second sub-chamber back toward the first sub-chamber during the axially-reciprocal shaking of the tube assembly, and wherein the impact surfaces of the flow disrupter are impacted by the sample before the flow-constricting passageway receives the sample during the axially-reciprocal shaking of the tube assembly.

17. The laboratory homogenizer tube assembly of claim 16, wherein:

the sample impacting against the impact surfaces and flowing through the flow-constricting passageway produces particle-size reduction of the sample by mechanical shear stress, pressure differentials, fluid shear stress, or cavitation, or a combination thereof, without a need to use grinding media in the tube chamber, the homogenizer produces the axially-reciprocal shaking of the tube assembly at higher speeds, for longer time periods, or with more-uniform controlled reliability, or a combination thereof, than by hand-shaking, the flow-constricting passageway is generally axially oriented within the tube chamber, the impact surfaces are impacted by the sample before the flow-constricting passageway receives the sample during the axially-reciprocal shaking of the tube assembly, or a total volume of the tube chamber includes a first volume of a first one of the sub-chambers defined by the flow disrupter and a second volume of a second one of the sub-chambers defined by the flow disrupter, and wherein the second sub-chamber volume is at least about 20 percent of the chamber total volume.

18. The laboratory homogenizer assembly of claim 16, wherein at least one of the flow-interrupting surfaces of the flow disrupter includes at least one generally perpendicular surface portion, and wherein at least one of the flow-interrupting surfaces of the flow disrupter includes at least one ramped surface portion that is generally conically shaped, that is concentric to and surrounded by the generally perpendicular surface portion, and that is concentric to and surrounds the flow passageway.

19. The laboratory homogenizer tube assembly of claim 16, wherein at least one of the flow-interrupting surfaces of the flow disrupter includes at least one generally perpendicular surface portion, and wherein:

at least one of the flow-interrupting surfaces of the flow disrupter includes at least one axially-extending annular fin surrounding the flow passageway and extending axially from the generally perpendicular surface portion; or the at least one flow-constricting passageway through the flow-interrupting body comprises a plurality of flow-constricting passageways formed through the flow-interrupting body, each of the flow-constricting passageways oriented parallel to the longitudinal axis of the tube chamber and defined in part by a ramped surface portion that is generally conically shaped, surrounding the respective flow passageway, at least partially surrounded by the generally perpendicular surface portion, and forms at least one of the flow-interrupting surfaces.

20. A laboratory homogenizing system for homogenizing a sample, the system comprising:

a laboratory homogenizer that generates an axially-reciprocal shaking motion; and a laboratory homogenizer tube assembly that mounts to the laboratory homogenizer for homogenizing the sample by the axially-reciprocal shaking motion, the tube assembly comprising:

two shell components that removably couple together to form an internal tube chamber with a longitudinal axis, a flow disrupter including a flow-interrupting body that extends generally transversely to the tube-chamber axis and into the tube chamber to divide the tube chamber into two axially-aligned sub-chambers, the body including at least two flow-interrupting impact surfaces and at least one flow-constricting passageway, wherein the at least one flow-constricting passageway is defined at least in part by and extends between the two flow-interrupting impact surfaces, has a cross-sectional flow area that is less than a cross-sectional flow area of the two sub-chambers, and forms a path for the sample to flow generally axially between the two sub-chambers in an accelerating then decelerating sequence in response to the axially-reciprocal shaking of the tube assembly, and wherein the at least two flow-interrupting impact surfaces are generally oppositely arranged on the flow-interrupting body facing in generally opposite axial directions, and wherein the two shell components cooperate with the two flow-interrupting impact surfaces to define the two sub-chambers, so that a first one of the impact surfaces is impacted by the sample as the sample flows in a first axial direction in a first one of the sub-chambers toward a second one of the sub-chambers, and a second one of the impact surfaces is impacted by the sample as the sample flows in a second axial direction in the second sub-chamber back toward the first sub-chamber during the axially-reciprocal shaking of the tube assembly.

* * * * *